United States Patent
Tobin, Jr. et al.

(10) Patent No.: US 6,535,776 B1
(45) Date of Patent: Mar. 18, 2003

(54) METHOD FOR LOCALIZING AND ISOLATING AN ERRANT PROCESS STEP

(75) Inventors: Kenneth W. Tobin, Jr., Harriman, TN (US); Thomas P. Karnowski, Knoxville, TN (US); Regina K. Ferrell, Knoxville, TN (US)

(73) Assignee: Ut-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/399,019

(22) Filed: Sep. 20, 1999

(51) Int. Cl.[7] .............................. G06F 19/00; G06K 9/00

(52) U.S. Cl. ...................... 700/110; 700/109; 700/121; 382/149

(58) Field of Search .................... 700/108–110, 121, 700/51; 382/141, 145, 149, 228; 702/84, 180, 185; 707/6

(56) References Cited

U.S. PATENT DOCUMENTS

| | | | |
|---|---|---|---|
| 5,129,009 A | 7/1992 | Lebeau | |
| 5,751,286 A | 5/1998 | Barber et al. | 345/835 |
| 5,761,064 A * | 6/1998 | La et al. | 700/110 |
| 5,787,190 A | 7/1998 | Peng et al. | |
| 5,793,888 A | 8/1998 | Delanoy | 382/219 |
| 5,819,288 A | 10/1998 | De Bonet | 707/2 |
| 5,862,055 A | 1/1999 | Chen et al. | |
| 5,893,095 A | 4/1999 | Jain et al. | 707/6 |
| 5,907,628 A | 5/1999 | Yolles et al. | |
| 5,940,300 A | 8/1999 | Ozaki | |
| 5,982,920 A * | 11/1999 | Tobin, Jr. et al. | 382/145 |
| 6,108,647 A * | 8/2000 | Poosala et al. | 707/1 |
| 6,148,268 A * | 11/2000 | Wu et al. | 702/84 |
| 6,202,037 B1 * | 3/2001 | Hattori et al. | 702/182 |
| 6,292,582 B1 * | 9/2001 | Lin et al. | 382/149 |

OTHER PUBLICATIONS

"Content–Based Image Retrieval Systems," Gudivada and V.V. Raghavan, IEEE Computer Magazine, 0018–9162, Sep. 1995, p. 18.

"Indexing Pictorial documents By Their Content: A Survey of Current Techniques," Imaging and Vision Computing, M.De Marsicoi, L. Cinque , and S. Levialdi, vol. 15, 1997, p. 119.

"A Knowledge–Based Approach for Retrieving Images by Content", IEEE Transactions on Knowledge and Data Engineering, Chih–Cheung Hsu, Wesley W. Chu, Ricky K. Taira, vol. 8, No. 4, Aug. 1996.

"Design of Large Intelligent Image Database Systems", vol. 11, 1996, p. 347.

"Image Retrieval and Pattern Recognition", SPIE, vol. 2916, 1996, p. 130.

* cited by examiner

Primary Examiner—Leo Picard
Assistant Examiner—Ryan Jarrett
(74) Attorney, Agent, or Firm—Akerman Senterfitt

(57) ABSTRACT

A method for localizing and isolating an errant process includes the steps of retrieving from a defect image database a selection of images each image having image content similar to image content extracted from a query image depicting a defect, each image in the selection having corresponding defect characterization data. A conditional probability distribution of the defect having occurred in a particular process step is derived from the defect characterization data. A process step as a highest probable source of the defect according to the derived conditional probability distribution is then identified. A method for process step defect identification includes the steps of characterizing anomalies in a product, the anomalies detected by an imaging system. A query image of a product defect is then acquired. A particular characterized anomaly is then correlated with the query image. An errant process step is then associated with the correlated image.

10 Claims, 6 Drawing Sheets

METHOD FOR LOCALIZING AND ISOLATING AN ERRANT PROCESS STEP

STATEMENT REGARDING FEDERALLY SPONSORED RESEARCH OR DEVELOPMENT

This invention was made with government support under contract DE-AC05-96OR22464, awarded by the United States Department of Energy to Lockheed Martin Energy Research Corporation. The United States government has certain rights in this invention.

CROSS REFERENCE TO RELATED APPLICATIONS (Not Applicable)

BACKGROUND OF THE INVENTION

1. Technical Field

This invention relates to the field of process step characterization and more particularly to a method and system for automatically localizing and isolating an errant process step using a content-based image retrieval engine and a historical defect characterization database.

2. Description of the Related Art

Recently, automation has played an increasingly more important role in manufacturing process monitoring, characterization, and control. Particularly, the availability of inexpensive, high-performance computing platforms in combination with digital signal processing technology has spurred the broad-based adoption of automatic defect inspection and classification systems for on-line, in-line and off-line product inspection and review. Automatic defect classification system typically are used to assess product quality at various points in the manufacturing process. The intent is to measure product quality on-line or in-line to facilitate the rapid discovery of errant process steps that are detracting from product quality. Consequently, automated inspection systems are required to reduce the need for a human operator to monitor the output of the inspection process.

Automated defect classification systems typically monitor a single process step and result in detecting, classifying, and reporting a pre-specified defect type. The defect pre-specification is determined based upon a training method related to inputting into the defect classification system a limited number of defect types associated with the process step under inspection. The defect classification system subsequently can attempt to detect and classify similar defects when placed in operation.

Notably, the placement of defect classification systems in multiple positions throughout an assembly line in manufacturing processes such as textile formation, textile printing, technical ceramic component manufacturing, printed circuit board manufacturing, and integrated circuit manufacturing generally results in the collection of an enormous volume of defect-related data. In particular, the defect-related data includes product images, defect classifications, tool associations, lot numbers and product specifications. In consequence, manufacturers store the collected data in large databases in an attempt to maintain a historical record of product and process quality issues. More particularly, manufacturers store the collected data with the intention of subsequently querying the database with present defect data in order to localize, isolate, and correct an errant manufacturing process step.

Notwithstanding, present methods cannot efficiently retrieve historical defect data from a database as a result of the enormous quantity of data stored therein. Specifically, present methods lack the ability to efficiently classify and retrieve defect imagery from a large defect database. Rather, present methods include either inaccurate computer retrieval of inconsistently characterized defect imagery or slow manual retrieval of defect imagery. Thus, an unsatisfied need exists for an efficient automated method for data mining defect imagery that can be used to statistically localize and isolate an errant process step.

SUMMARY OF THE INVENTION

A method for localizing and isolating an errant process step in accordance with the inventive arrangement satisfies the long-felt need of the prior art by integrating content-based image retrieval [CBIR] with a large, sorted database of defect imagery and corresponding defect characterization data to efficiently diagnose a defective product and identify an errant process apparatus causing the defective product. Using a CBIR engine, the present invention can compare image content extracted from a query image to image content extracted from a group of images. Generally, imagery sharing similar image content represent similar manufacturing conditions. Thus, the present invention extends manufacturing-specific CBIR by determining an estimate of a conditional probability that associates the query image with an errant tool and defect type. The inventive arrangements have advantages over all defective process step identification techniques, and provides a system and apparatus for errant process step identification based on content-based image retrieval.

A method for localizing and isolating an errant process step comprises the steps of: retrieving from a defect image database a selection of images, each image having image content similar to image content extracted from a query image depicting a defect, each image in the selection having corresponding defect characterization data; deriving from the defect characterization data a conditional probability distribution of the defect having occurred in a particular process step; and, identifying a process step as a highest probable source of the defect according to the derived conditional probability distribution.

In particular, the retrieving step comprises the steps of: providing to a content-based image retrieval engine, a query image depicting a defect; retrieving from the content-based image retrieval engine, a selection of images, each image having image content similar to image content extracted from the query image; and, ranking the selection of images according to a similarity metric.

The deriving step comprises the steps of: calculating a process step conditional probability distribution from the defect characterization data; calculating a defect class conditional probability distribution from the defect characterization data; selecting a process step included in the process step conditional probability distribution having a highest probability; selecting a defect class included in the defect class conditional probability distribution having a highest probability; and, merging the selected process step with the selected defect class to produce a probable source process step of the defect. Subsequently, the identifying step can comprise the steps of: ordering a ranked list of probable source process steps of the defect; and, reporting to a user the ranked list, whereby the ranked list localizes and isolates a probable source process step of the defect.

A method for process step defect identification comprises four steps. First, product anomalies can be characterized. Specifically, the product anomalies can be detected by an imaging system. Moreover, the characterizing step can comprise the steps of: detecting a product anomaly passing within imaging range of a computer vision system; forming an image of the product anomaly; assigning defect characterization data to the formed image; and, storing the formed image and the assigned image defect characterization in a defect characterization database, whereby each formed image and assigned image defect characterization in the defect characterization database can be retrieved for subsequent comparison to a query image depicting a product anomaly. Significantly, the assigning step comprises the step of assigning to the acquired image defect a defect class label and an associated process step. Furthermore, the storing step comprises the step of sorting each acquired image and assigned defect characterization data in a hierarchical search tree structure using an unsupervised clustering algorithm.

Second, a query image of a product defect can be acquired. The acquiring step can comprise the step of generating an image of a type selected from the group consisting of optical imagery, laser scattering imagery, interferogram imagery, scanning electron microscopy imagery, and atomic force microscopy imagery.

Third, a particular characterized anomaly can be correlated with the query image. The correlating step can comprise the steps of: retrieving from the defect characterization database, a selection of images, each image having image content similar to image content extracted from the query image; and, ranking the selection of images according to a similarity metric. In particular, the ranking step can comprise the steps of: retrieving from the defect characterization database, defect characterization data corresponding to the selection of images; deriving from the defect characterization data a conditional probability distribution of the defect having occurred in a particular process step; and, identifying a process step as a highest probable source of the defect according to the derived conditional probability distribution. More particularly, the deriving step can comprise the steps of: calculating a process step conditional probability distribution from the defect characterization data; calculating a defect class conditional probability distribution from the defect characterization data; selecting a process step included in the process step conditional probability distribution having a highest probability; selecting a defect class included in the defect class conditional probability distribution having a highest probability; and, merging the selected process step with the selected defect class to produce a probable source process step of the defect.

Finally, an errant process step associated with the correlated image can be isolated.

BRIEF DESCRIPTION OF THE DRAWINGS

There are presently shown in the drawings embodiments which are presently preferred, it being understood, however, that the invention is not limited to the precise arrangements and instrumentalities shown.

DETAILED DESCRIPTION OF THE INVENTION

The present invention relates to a method and apparatus which can exploit CBIR technology to automate the characterization of process steps in the manufacturing environment. CBIR systems are well known in the art, particularly as to the CBIR system's ability to effectively and efficiently retrieve images from large image repositories based upon the contents of the images contained therein. In practice, typical CBIR systems optically acquire images using well-known computer vision techniques, extract image features from the acquired images, in particular, image color, texture, sketch, shape volume, spatial constraints, and store the images in a database according to the extracted image features. Modern CBIR systems include integrated subsystems for image feature extraction and object-recognition. Specifically, these subsystems automate the feature-extraction and object-recognition task that occurs when an image is inserted into an image database. Subsequently, the CBIR system can retrieve an image or a collection of images from the database, each image sharing similar image content to the content of a query image. More particularly, the CBIR system can retrieve an image or a collection of images from the database, each image sharing matching image features, for example matching texture, color, spatial constraints, or any relevant combination of extracted image features. RetrievalWare® from Excalibur Technologies Corporation of Vienna, Va., represents one such commercially available CBIR system.

The present invention can employ a CBIR engine to retrieve a set of images from a historical database established for a manufacturing process through the use of on-line, in-line, and off-line defect inspection and characterization technology. The present invention can compare a query image to a group of visually similar images selected by the CBIR engine. Generally, imagery containing similar visual characteristics represent similar manufacturing conditions. Thus, the present invention extends manufacturing-specific CBIR by determining an estimate of a conditional probability that associates the query image with an errant tool and defect type. The result is a process step characterization system that automatically alerts the user to the existence of a quality detracting condition, in conjunction with the localization and isolation of the associated errant process step.

Figure 1:
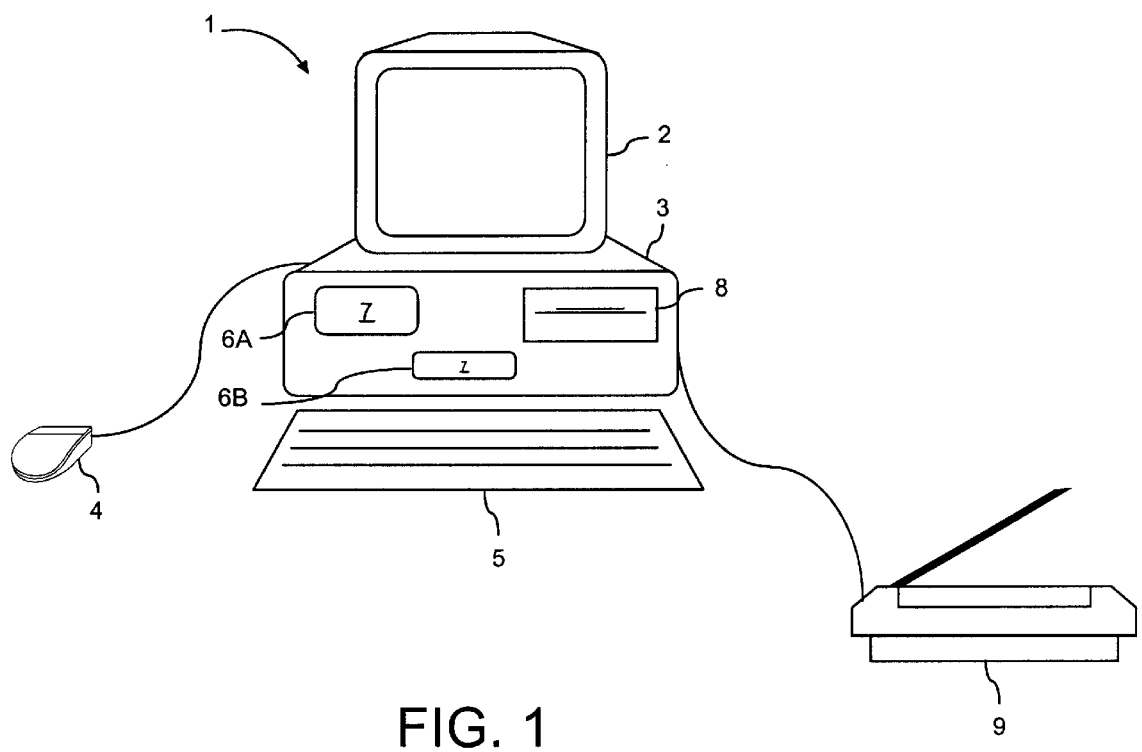
FIG. 1 is a pictorial representation of a computer system with mouse and imaging capabilities on which the apparatus of the invention can be used.

FIG. 1 shows a typical computer system 1 for use in conjunction with the present invention. The system preferably comprises a computer 3 having a central processing unit (CPU), fixed disk 6A, internal memory device 6B, and CD-ROM drive 8. The system also includes a keyboard 5, and at least one user interface display unit 2 such as a video data terminal (VDT) operatively connected thereto. The CPU can be comprised of any suitable microprocessor or other electronic processing unit, as is well known to those skilled in the art. An example of such a CPU would include the Pentium or Pentium II brand microprocessor available from Intel Corporation, or any similar microprocessor. An interface device, such as mouse 4, can also be provided with the system, but is not necessary for operation of the invention as described herein. Finally, the system 1 preferably includes computer imaging system 9 for visually acquiring an image for processing by the system 1. The various hardware requirements for the computer system as described herein can generally be satisfied by any one of many commercially available high speed personal computers offered by manufacturers such as International Business Machines (IBM), Compaq, Hewlett Packard, or Apple Computers.

Figure 2:
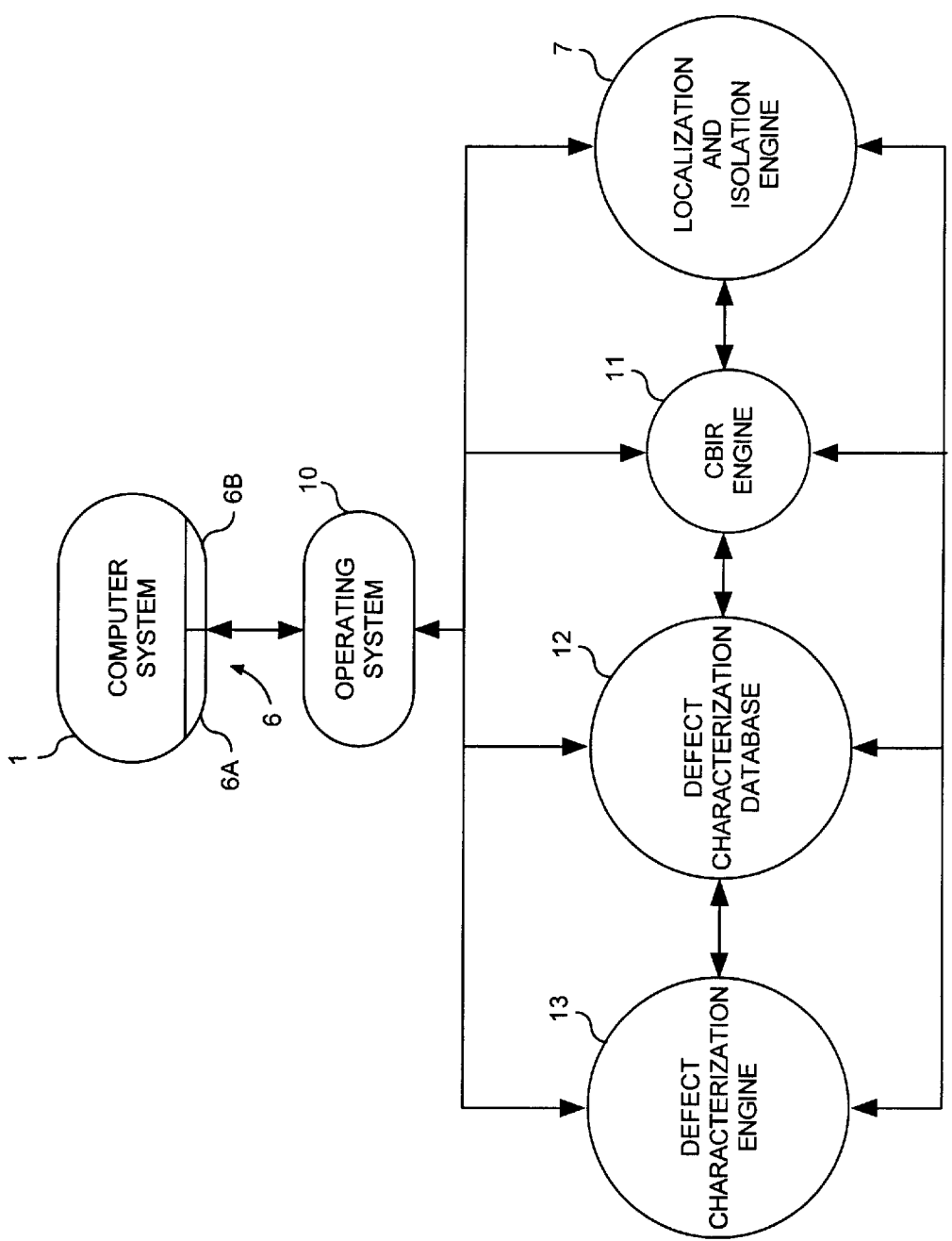
FIG. 2 is a block diagram showing a typical high level architecture for the computer system in FIG. 1.

FIG. 2 illustrates a preferred architecture for an automatic errant process step localization and isolation apparatus in computer 1. As shown in FIG. 2, computer system 1 includes one or more computer memory devices 6, preferably an electronic random access memory 6B and a bulk data storage medium, such as a fixed disk drive 6A. In addition, the apparatus can include an operating system 10, a CBIR engine 11, a defect characterization database 12, a defect characterization engine 13, and a localization and isolation engine 7 in accordance with the inventive arrangements. In FIG. 2, the localization and isolation engine 7, CBIR engine 11, defect characterization database 12 and defect characterization engine 13 are shown as separate application programs. It should be noted, however, that the invention is not limited in this regard, and these various applications could, of course, be implemented as a single, more complex applications program.

In a preferred embodiment described herein, operating system 10 is one of the Windows family of operating systems, such as Windows NT, Windows 95 or Windows 98 which are available from Microsoft Corporation of Redmond, Wash. However, the system is not limited in this regard, and the invention can also be used with any other type of computer operating system, for instance the Linux operating system, freely available from a variety of commercial and non-commercial sources, for instance the Internet web site, "http://www.linux.org".

The preferred process preferably can be implemented using the C++ language. In consequence, the source code comprising the inventive apparatus can be compiled and interpreted using any one of several commercial and non-commercial C++ compilers, for instance Visual C++®, commercially available from Microsoft Corporation. In addition, the defect classification database can be any commercially available database, for instance, Microsoft Access®, Adaptive Server Anywhere® developed by Sybase of Emeryville, Calif., or ORACLE 8® developed by Oracle of Redwood Shores, Calif. The inventive apparatus can interface with the defect classification database through a transportability algorithm, developed using a cross-platform C++ database accessibility toolkit, for example dbtools.h++® from Rogue Wave Software of Boulder, Colo., and compiled into a dynamic-link library.

Figure 3:
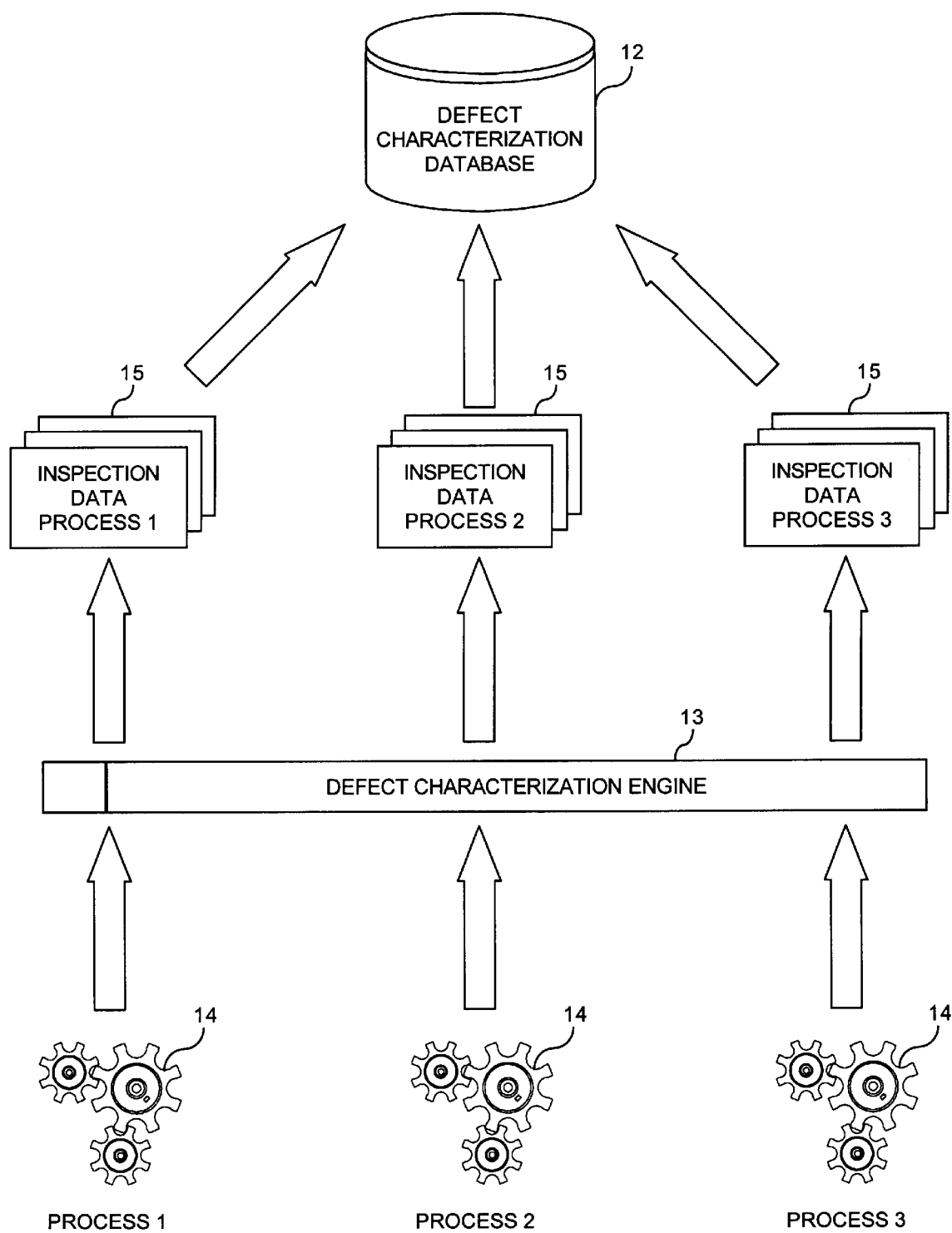
FIG. 3 is a schematic representation of an automatic defect characterization system according to the inventive arrangements.

FIG. 3 is a schematic representation of an automatic defect characterization system according to the inventive arrangements. Specifically, FIG. 3 represents the manufacturing process where a generic product experiences several manufacturing process steps 14 represented as "Process 1", "Process 2", and "Process 3". More particularly, the product undergos a process step 14, which can in itself, be composed of several process sub-steps, to add value towards manufacturing a finished item. Recognizably, the process step 14 can also impart a deviation form the desired product characteristic at any time as a result of a tool or equipment fault, or process step parameter drift. Consequently, manufacturers implement inspection strategies.

In the present invention, the preferred defect inspection strategy includes defect characterization. System 1 includes a defect characterization engine 13 which can employ computer vision technologies to generate a viewable and storable image record of each product under inspection. Notably, computer vision inspection systems can generate optical images, laser scattering images, interferograms, scanning electron microscopy images, atomic force microscopy images, and a host of other modalities that represent the product under inspection. These inspection modalities and systems provide digital representations for subsequent processing, analysis, and archiving.

A capability of inspection that relates to the present invention is the ability of a computer vision system to automatically characterize anomalies that are detected in the field of view of the imaging system. Characterization is the step by which a detected defect is assigned a defect class label that describes the subject product's morphology, material characteristics, potential product impact, and location. The automatic characterization of anomalies often is referred to as automatic defect characterization. In the preferred embodiment, automatic defect characterization represents the characterization of the product under inspection. Notwithstanding, one skilled in the art will recognize that one could substitute automated defect characterization for manual defect characterization. That is to say, an individual could inspect a defect image and manually input the defect characteristics into a database to be stored along with the defect image.

Each defect class label, formed by defect characterization engine 13, can be combined with an association with a process step 14 and other information such as the product type or lot number, and encapsulated by an inspection data record 15. The inspection data record 15 can be maintained in defect characterization database 12 for subsequent analysis and control. As a result, the process step 14 information can facilitate automated process step characterization, while the defect class label can facilitate automated product characterization. Significantly, in consequence of the storage of defect characterization data in addition to defect imagery, the present invention can provide to a user not only a list of imagery similar to an image of defective product, but also a statistically valid estimate of the probable cause of the defect in the defective product.

Figure 4:
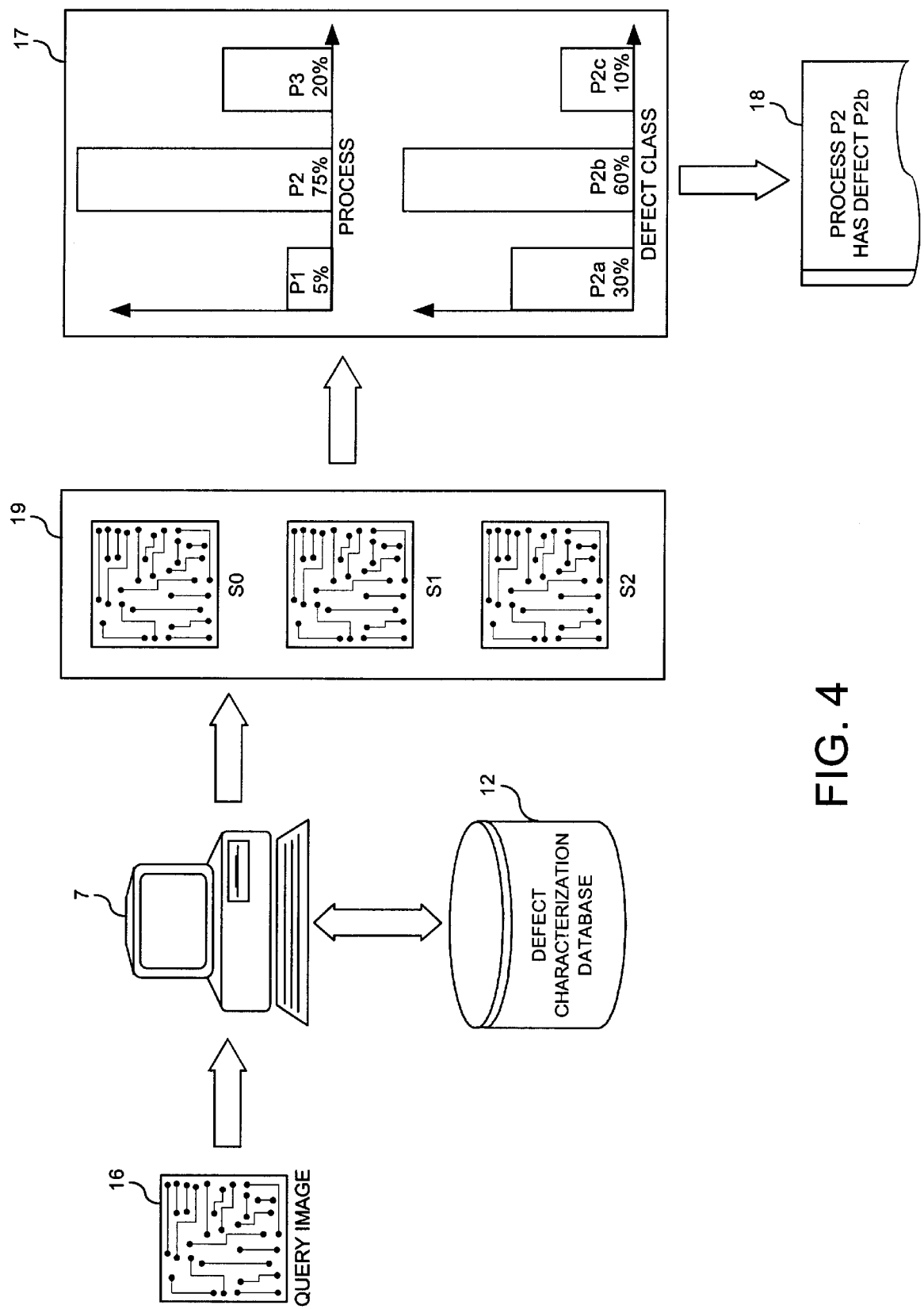
FIG. 4 is a schematic representation of an apparatus for localizing and isolating an errant process step according to the inventive arrangements.

FIG. 4 is a schematic representation of an apparatus for localizing and isolating an errant process step 14 according to the inventive arrangements. In FIG. 4, a user can submit to the localization and isolation engine 7 a query image 16 taken from the inspection process. In particular, query image 16 represents a problem identified by one of the manufacturing inspection systems. The user can provide the query image 16 to the localization and isolation engine 7 through computer imaging system 9. The localization and isolation engine 7 can pass the query image 16 to the CBIR engine 11. The CBIR engine 11 can query defect characterization database 12 and return a list of inspection data records 15 having defect imagery and defect characterization data. From the list, the localization and isolation engine 7 can extract a selection of images 19 $\{n\}$ with $n=0,1 \ldots N-1$, each inspection data record 15 having an image visually similar to the query image 16.

The selection of images 19 preferably are ranked according to a similarity metric such that the first returned image in the selection of images 19 is most similar to the query image 16, the second is the next most similar, etc. The similarity metric $s_n$, $n=0, 1 \ldots N-1$ for N number of images returned by the query, is a value that ranges over the interval [0,1], where similarity equals 1 for an exact match, or 0 for a complete mismatch. In view of the correlation between similar visual characteristics and similar manufacturing conditions, the similarity metric can be described as a measure of confidence in the estimate that the retrieved image was caused by a similar manufacturing event.

The inspection data records 15 retrieved from the defect characterization database 12 contains within it a sample of the process steps 14 that are associated with the errant condition that caused the formation of the defect in the query image 16. In a statistical sense, the selection of similar images and associated process step information encapsulated by inspection data records 15 represent a conditional probability distribution 17. For example, the conditional probability distribution 17 in FIG. 3 indicates a 75% occurrence of the process step "p2" among the population of images having similar visual appearance to the query image 16. Of the images retrieved that are related to process step p2, the defect class histogram shows a 60% occurrence of the defect class "p2b" in the specified population. Subsequently, the user preferably is sent a report specifying the probable cause of the manufacturing problem. Alternatively, the user can be sent a ranked listing of probable causes. In particular, each cause can be ranked according to the conditional probability 17 reported by the statistical analysis.

Figure 5A:
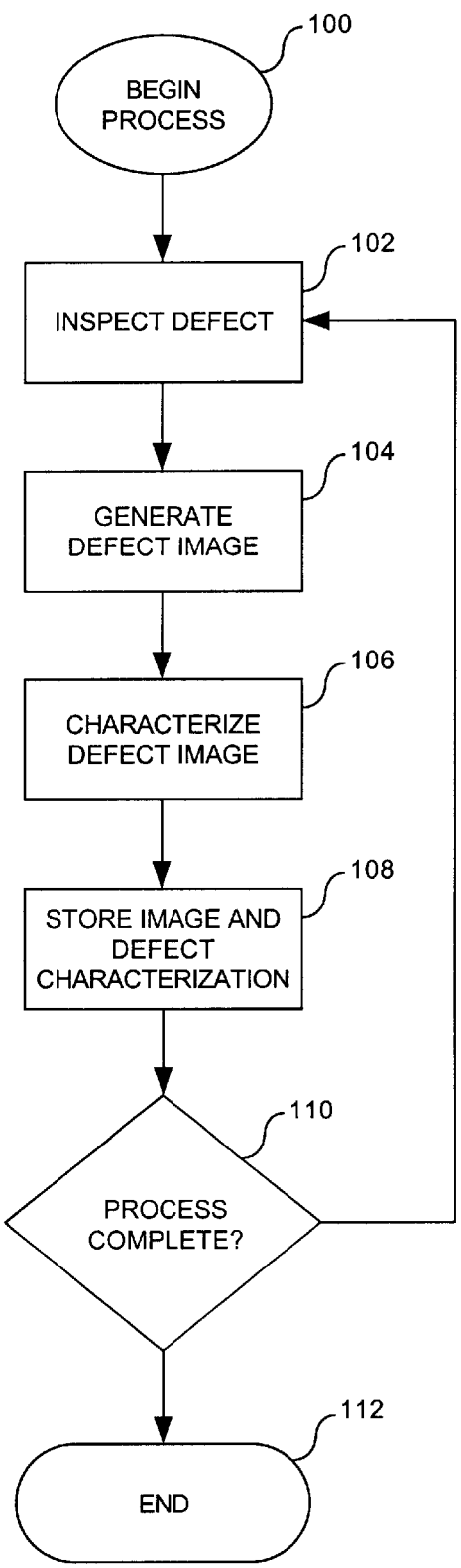
FIGS. 5A–5B, taken together, is a flow chart illustrating a method for localizing and isolating an errant process step.
Figure 5B:
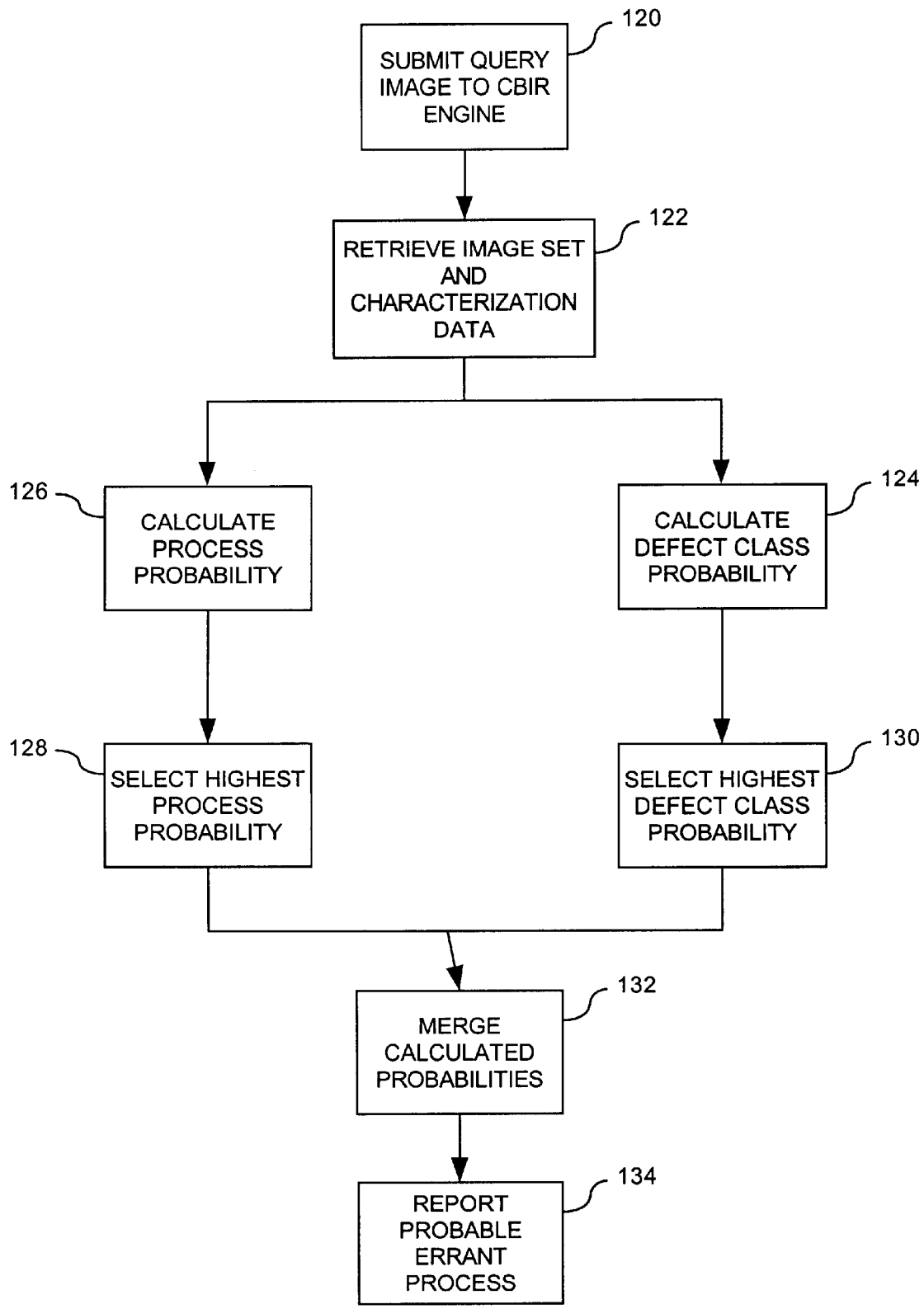

FIGS. 5A–5B, taken together, is a flow chart illustrating a method for localizing and isolating an errant process step. FIG. 5A depicts a process for automatically characterizing defect imagery. The process begins in step 100 leading to step 102. In step 102, a product under manufacture can be visually inspected by a computer vision system. In consequence, in step 104 a defect image can be formed by the computer vision system. In step 106, defect characterization engine 13 can characterize the defect image. Specifically, defect characterization engine 13 can generate a defect class label. In addition, defect characterization engine 13 can associate the defect image with a process step 14. Finally, defect characterization engine 13 can encapsulate the defect image, defect class label and process step association in an inspection data record 15. In step 108, defect characterization engine 13 can store the inspection data record 15 in defect characterization database 12 for subsequent analysis and control. Advantageously, according to an efficient CBIR design, each inspection data record 15 can be inserted into a hierarchical search tree and indexed using an unsupervised clustering method. In decision step 110, the process can repeat for each additional inspected product before exiting in step 112.

FIG. 5B depicts a process for localizing and isolating an errant process. Beginning with step 120, a user can submit a query image 16 to localization and isolation engine 7, the query image 16 having been acquired by computer imaging system 9. The localization and isolation engine 7 can pass the query image 16 to the CBIR engine 11. The CBIR engine 11 can query defect characterization database 12 and return a list of inspection data records 15 having defect imagery and defect characterization data. From the list, the localization and isolation engine 7 can extract a selection of images 19 {n} with n=0,1 ... N–1, each inspection data record 15 having an image visually similar to the query image 16.

The selection of images 19 preferably are ranked according to a similarity metric such that the first returned image in the selection of images 19 is most similar to the query image 16, the second is the next most similar, etc. The similarity metric $s_n$, n=0,1 ... N–1 for N number of images returned by the query, is a value that ranges over the internal [0,1], where similarity equals 1 for an exact match, or 0 for a complete mismatch.

In step 124, the conditional probability P of a defect in a query image $I_q$ 16 having been caused by a particular process step 14 $p_m$ can be characterized by the following probability distribution:

$$P(p_m|I_q) \approx \frac{\sum_{n=0}^{N-1} s_n \cdot (p_n = p_m)}{\sum_{n=0}^{N-1} s_n}, \forall\, p_m, m = 0, 1 \ldots M-1$$

where, $P_n = P_m$ is 1 if true and 0 if false.

Similarly, in step 126, the conditional probability P of a defect in a query image $I_q$ 16 having a particular defect class $c_k$ can be characterized by the following probability distribution:

$$P(c_k|I_q) \approx \frac{\sum_{n=0}^{N-1} s_n \cdot (c_n = c_k)}{\sum_{n=0}^{N-1} s_n}, \forall\, c_k, k = 0, 1 \ldots K-1$$

where, $c_n = c_k$ is 1 if true and 0 if false. Notably, for both probability calculations, similarity metric $s_n$ is used as a weighting factor to give more importance to imagery that is most similar to the query image 16.

In step 130, the highest probability for the defect class is identified. Likewise, in step 128, the highest probability for a process step 14 is identified. In step 132, both are merged to produce a probable defect class having occurred in a probable errant process step 14. The identified probable defect class and probable errant process step 14, in step 134, can be reported to the user either in the form of a conclusion, or in a ranked list of likely defect classes and errant process steps 14.

In consequence of the present invention, once an extensive defect characterization database 12 has been established, an automated query system can be implemented that receives an query image 16 from an inspection system, and performs a query and process step characterization procedure by automatically submitting the inspection system imagery to the localization and isolation engine 7. Hence, a human user is not required to interact with the query loop, other than to receive final reporting and recommendation. Thus, the present invention provides an efficient automated method for retrieving defect characterization data, particularly defect imagery that is subsequently used to localize and isolate an errant process step.

What is claimed is:

1. A method for localizing and isolating an errant process step in multi-step processes, comprising the steps of:

retrieving from a defect image database a selection of images, each said image having image content similar to image content extracted from a query image depicting a defect, each said image in said selection having corresponding defect characterization data; and directly deriving from said defect characterization data a conditional probability distribution of said defect having occurred in at least one process step; wherein a particular process step from said process steps can be identified as a highest probable source of said defect based on said conditional probability distribution.

2. The method according to claim 1, wherein the retrieving step comprises the steps of:

providing to a content-based image retrieval engine, a query image depicting a defect;

retrieving from said content-based image retrieval engine, a selection of images, each said image having image content similar to image content extracted from said query image; and, ranking said selection of images according to a similarity metric.

3. The method according to claim 1, wherein the deriving step comprises the steps of:

calculating a process step conditional probability distribution from said defect characterization data;

calculating a defect class conditional probability distribution from said defect characterization data;

selecting a process step included in said process step conditional probability distribution having a highest probability;

selecting a defect class included in said defect class conditional probability distribution having a highest probability; and, merging said selected process step with said selected defect class to produce a probable source process step of said defect.

4. The method according to claim 1, wherein the identifying step comprises the steps of:

ordering a ranked list of probable source process steps of said defect; and, reporting to a user said ranked list, whereby said ranked list localizes and isolates a probable source process step of said defect.

5. A method for process step defect identification comprising the steps of:

characterizing anomalies in a product said anomalies detected by a content-based imaging system, wherein the characterizing step comprises the steps of detecting a product anomaly passing within imaging range of a computer vision system; forming an image of said product anomaly; assigning defect characterization data to said formed image; and, storing said formed image and said assigned image defect characterization in a defect characterization database, whereby each formed image and assigned image defect characterization in said defect characterization database can be retrieved for subsequent comparison to a query image depicting a product anomaly;

acquiring a query image of a product defect;

correlating a particular characterized anomaly with said query image, wherein the correlating step comprises the steps of retrieving from said defect characterization database, a selection of images, each image having image content similar to image content extracted from said query image; ranking said selection of images according to a similarity metric wherein the ranking step comprises the steps of: retrieving from said defect characterization database, defect characterization data corresponding to said selection of images; deriving from said defect characterization data a conditional probability distribution of said defect having occurred in a particular process step; and, identifying a process step as a highest probable source of said defect according to said derived conditional probability distribution, and, identifying an errant process step associated with said correlated image.

6. The method according to claim 5, wherein the deriving step comprises the steps of:

calculating a process step conditional probability distribution from said defect characterization data;

calculating a defect class conditional probability distribution from said defect characterization data;

selecting a process step included in said process step conditional probability distribution having a highest probability;

selecting a defect class included in said defect class conditional probability distribution having a highest probability; and, merging said selected process step with said selected defect class to produce a probable source process step of said defect.

7. A computer apparatus programmed with a routine set of instructions stored in a fixed medium comprising:

means for retrieving from a defect image database a selection of images, each image having image content similar to image content extracted from a query image depicting a defect, each said image in said selection having corresponding defect characterization data;

means for directly deriving from said defect characterization data a conditional probability distribution of said defect having occurred in at least one process step; and, means for identifying a process step as a highest probable source of said defect based on said derived conditional probability distribution.

8. The computer apparatus according to claim 7, wherein the retrieving means comprises:

means for providing to a content-based image retrieval engine, a query image depicting a defect;

means for retrieving from said content-based image retrieval engine, a selection of images, each image having image content similar to image content extracted from said query image; and, means for ranking said selection of images according to a similarity metric.

9. The computer apparatus according to claim 7, wherein the deriving means comprises:

means for calculating a process step conditional probability distribution from said defect characterization data;

means for calculating a defect class conditional probability distribution from said defect characterization data;

means for selecting a process step included in said process step conditional probability distribution having a highest probability;

means for selecting a defect class included in said defect class conditional probability distribution having a highest probability; and, means for merging said selected process step with said selected defect class to produce a probable source process step of said defect.

10. The computer apparatus according to claim 7, wherein the identifying means comprises:

means for ordering a ranked list of probable source process steps of said defect; and, means for reporting to a user said ranked list, whereby said ranked list localizes and isolates a probable source process step of said defect.

* * * * *